United States Patent [19]

Södervall et al.

[11] Patent Number: 4,556,677
[45] Date of Patent: Dec. 3, 1985

[54] ALKANE AND ALKENE DERIVATIVES AND THEIR USE

[75] Inventors: Marja-Liisa Södervall; Kauko O. A. Kurkela; Arto J. Karjalainen; Reijo J. Toivola, all of Oulu; Lauri V. M. Kangas, Turku; Guillermo L. Blanco, Oulu, all of Finland

[73] Assignee: Farmos Group Ltd., Turku, Finland

[21] Appl. No.: 436,805

[22] Filed: Oct. 26, 1982

[30] Foreign Application Priority Data

Oct. 26, 1981 [GB] United Kingdom ............... 8132240

[51] Int. Cl.$^4$ ........................................ C07C 43/205
[52] U.S. Cl. ................................. 514/651; 549/549; 564/347; 568/631
[58] Field of Search .................... 560/108; 514/651; 549/549; 568/631

[56] References Cited

FOREIGN PATENT DOCUMENTS 0078158 5/1983 European Pat. Off. .
1963271 7/1970 Fed. Rep. of Germany .

OTHER PUBLICATIONS

Dore, J. C. et al., C. R. Seances Acad. Sci., Ser. 2, 293(15), 1061–4, 1981.

Primary Examiner—Paul J. Killos
Attorney, Agent, or Firm—Armstrong, Nikaido, Marmelstein & Kubovcik

[57] ABSTRACT

The invention provides novel compounds of the formula

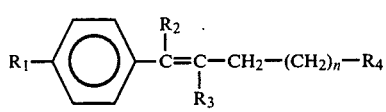

(I)

or

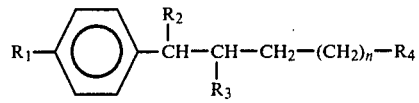

(II)

wherein $R_1$ is hydrogen, hydroxy, alkoxy of 1 to 4 carbon atoms, benzyloxy, allyloxy, 2,3-epoxypropoxy, methoxymethoxy, ethoxymethoxy, or 2,3-dihydroxypropoxy or

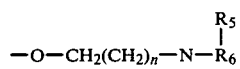

wherein one of $R_5$ and $R_6$ is hydrogen or $R_5$ and $R_6$ are alkyl groups of 1-4 carbon atoms which may be the same or different, or the $-NR_5R_6$ group stands for a nitrogen containing 5 to 7 membered heterocyclic radical and m is 1 or 2; $R_2$ is an alkyl of 1 to 4 carbon atoms or

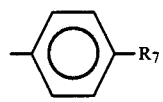

wherein $R_7$ has the same meanings as $R_1$ except that $R_7$ and $R_1$ cannot simultaneously be the same; $R_3$ is an alkyl of 2 to 4 carbon atoms, cyclopentyl or hydroxy-cyclopentyl; $R_4$ is hydrogen or hydroxy; and n is 0 to 3, provided that when $R_4$ is hydrogen, then $R_2$ and $R_3$ are not simultaneously lower alkyl containing up to 4 carbon atoms, and their non-toxic pharmaceutically acceptable acid addition salts and esters and mixtures thereof. Processes for the preparation of these compounds are described, as are novel pharmaceutical compositions of the compounds or their salts. The compounds and their non-toxic salts exhibit valuable pharmacological properties as estrogenic, anti-estrogenic, progestanic and anti-tumor activity. Certain compounds of the group are useful as chemical intermediates for the preparation of pharmaceutically active compounds of the invention.

26 Claims, No Drawings

ALKANE AND ALKENE DERIVATIVES AND THEIR USE

DESCRIPTION

The present invention relates to novel alkane and alkene derivatives and their non-toxic pharmaceutically acceptable salts and esters, and their preparation, to pharmaceutical compositions containing the same and to their use.

The compounds of the present invention have the general formula:

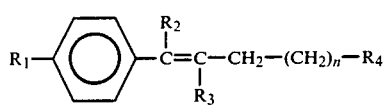  (I)

or

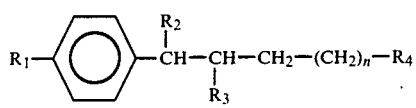  (II)

wherein $R_1$ is hydrogen, hydroxy, alkoxy of 1 to 4 carbon atoms, benzyloxy, allyloxy, 2,3-epoxypropoxy, 2,3-dihydroxypropoxy, methoxymethoxy, ethoxymethoxy or

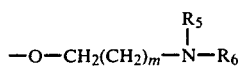

wherein one of $R_5$ and $R_6$ is hydrogen or $R_5$ and $R_6$ are alkyl groups of 1–4 carbon atoms which may be the same or different or the $-NR_5R_6$ group stands for a nitrogen containing 5 to 7 membered heterocyclic radical and m is 1 or 2; $R_2$ is an alkyl of 1 to 4 carbon atoms or

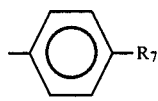

wherein $R_7$ has the same meanings as $R_1$ except that $R_7$ and $R_1$ cannot simultaneously be the same; $R_3$ is an alkyl of 2 to 4 carbon atoms, cyclopentyl or hydroxycyclopentyl; $R_4$ is hydrogen or hydroxy and n is 0 to 3 provided that when $R_4$ is hydrogen, then $R_2$ and $R_3$ are not simultaneously lower alkyl containing up to 4 carbon atoms.

The above definition encompasses stereoisomers of the compounds in question and mixtures thereof.

The non-toxic pharmaceutically acceptable salts of these compounds are also within the scope of the invention.

The invention relates to pharmaceutically acceptable salts of aminosubstituted compounds with organic and inorganic acids, for example citric acid and hydrochloric acid. The invention includes further pharmaceutically acceptable salts, which can be prepared from the phenolic compounds by treatment with inorganic bases, e.g. sodium hydroxide. Further the invention includes esters with aliphatic and aromatic carboxylic acids, e.g. acetic and benzoic acid.

The invention includes with its scope pharmaceutical compositions comprising at least one of the compounds of formula (I) and (II) or a non-toxic, pharmaceutically acceptable salt or ester thereof, and a compatible pharmaceutically acceptable carrier thereof.

While all of the compounds of formula (I) and (II) essentially satisfy the objectives of the present invention, certain groups of compounds remain preferred. One such preferred group is represented by formula (I) and (II) wherein $R_3$ is cyclopentyl or hydroxycyclopentyl. Especially preferred compounds are represented by formula (I) wherein $R_2$ is

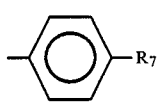

and $R_3$ is cyclopentyl or hydroxycyclopentyl.

The present invention provides, for example, the following specific compounds of formula (I) and (II):
2-cyclopentyl-1-(p-hydroxyphenyl)-1-phenyl-1-butene
2-cyclopentyl-1-(p-methoxyphenyl)-1-phenyl-1-butene
2-cyclopentyl-1-[p-(N,N-dimethyl-2-aminoethoxy)-phenyl]-1-p-methoxyphenyl-1-butene
2-cyclopentyl-1-[p-(N,N-dimethyl-2-aminoethoxy)-phenyl]-1-phenyl-1-butene
2-ethyl-3-(p-methoxyphenyl)-3-phenyl-2-propen-1-ol
2-ethyl-3-(p-methoxyphenyl)-1-pentanol
2-ethyl-3-(p-hydroxyphenyl)-1-pentanol
2-ethyl-3-(p-hydroxyphenyl)-3-phenyl-2-propen-1-ol
3-cyclopentyl-4-(p-methoxyphenyl)hexane
3-cyclopentyl-4-(p-hydroxyphenyl)hexane
2-cyclopentyl-1-(p-methoxyphenyl)-1-phenylbutane
2-cyclopentyl-1-(p-hydroxyphenyl)-1-phenylbutane
2-(3-hydroxy-1-cyclopentyl)-1-(p-methoxyphenyl)-1-phenyl-1-butene
2-(3-hydroxy-1-cyclopentyl)-1-(p-hydroxyphenyl)-1-phenyl-1-butene
2-(3-hydroxy-1-cyclopentyl)-1-[p-(N,N-dimethyl-2-aminoethoxy)phenyl]-1-phenyl-1-butene
2-cyclopentyl-1-[p-(N,N-dimethyl-2-aminoethoxy)-phenyl]-1-(p-hydroxyphenyl)-1-butene
2-cyclopentyl-1-[p-(N,N-diethyl-2-aminoethoxy)-phenyl]-1-phenyl-1-butene
2-cyclopentyl-1-[p-(N-methyl-2-aminoethoxy)phenyl]-1-phenyl-1-butene
2-cyclopentyl-1-(p-allyloxyphenyl)-1-phenyl-1-butene
2-cyclopentyl-1-[p-(2,3-epoxypropoxy)phenyl]-1-phenyl-1-butene
2-cyclopentyl-1-[p-(2,3-dihydroxypropoxy)phenyl]-1-phenyl-1-butene According to a feature of the invention, the compounds of formula (I) can be prepared according to a process wherein an arylalkyl ketone of the formula

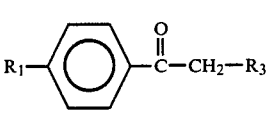  (III)

wherein $R_1$ is as defined before or mixed acetal, e.g. tetrahydropyranyloxy, and $R_3$ is as defined before, is alkylated in the presence of a strong base, such as sodium hydride, with an alkyl halide of the formula

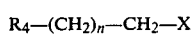  (IV)

wherein R₄ is as defined before or benzyloxy or mixed acetal, e.g. tetrahydropyranyloxy radical, X is halogen and n is as defined before, to give a ketone of the formula

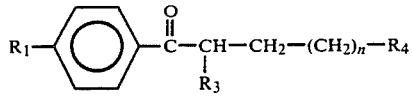
(V)

where $R_1$, $R_3$, $R_4$ and n are as above. The compounds of the formula (V), wherein $R_1$ is alkoxy can be dealkylated, e.g. with aluminum trichloride, to the corresponding compounds wherein $R_1$ is hydroxy. Preferably the dealkylation is performed at this stage because of the stimulating effect of the p-carbonyl group.

The ketone of the formula (V) is reacted with an organometallic compound of the formula $R_2MgX$ or $R_2Li$, wherein $R_2$ is as defined before and X is halogen, to give a hydroxy compound of the formula

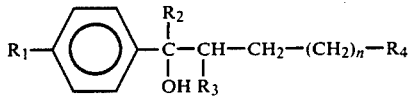
(VI)

where $R_2$, $R_3$ and n are as defined before, $R_1$ and $R_4$ are as defined before or contain the above mentioned protecting groups.

The benzylic alcohol of the formula (VI) is dehydrated for example in the presence of an acid, e.g. HCl, HCOOH, CF₃COOH, KHSO₄ or p-toluenesulfonic acid, to produce a vinylbenzene of the formula

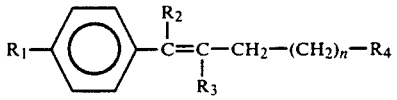
(VII)

wherein $R_1$, $R_2$, $R_3$, $R_4$ and n are as in (VI). To produce compounds (I) the possible protecting groups in $R_1$ and $R_4$ can be removed before dehydration, simultaneously with dehydration or after it depending on the used method. Preferably the possible benzylic group in $R_4$ is removed by catalytic hydrogenation before dehydration process.

Another way to produce compounds of the formula (I) is the O-alkylation of the corresponding phenolic compounds of the formula

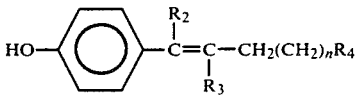
(VIII)

wherein $R_2$, $R_3$, $R_4$ and n are as before, in basic conditions with an alkyl or a benzyl halide of the formula $R_8X$, where X is halogen and $R_8$ is lower alkyl, benzyl, allyl, 2,3-epoxypropyl, 2,3-dihydroxypropyl, alkoxyalkyl or —CH₂(CH₂)ₘNR₅R₆, wherein m, $R_5$ and $R_6$ are as defined before, to give phenylethers of the formula

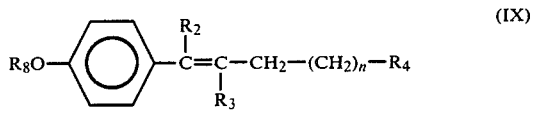
(IX)

wherein $R_2$, $R_3$, $R_4$, $R_8$ and n are as before. The method to produce basic O-alkylation products can also be performed in two phases: First the phenolic compound of the formula (VIII) can be alkylated with a dihaloalkane X—CH₂(CH₂)ₘX, where m is as before and X are halogen atoms, which can be the same or different, to give a (p-haloalkoxyphenyl)alkene of the formula

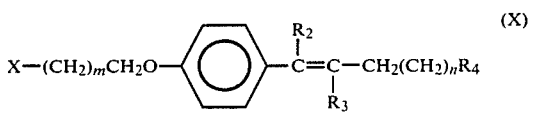
(X)

wherein $R_2$, $R_3$, $R_4$, n and m are as defined before and X is halogen, after which the halogen atom X can be replaced with a primary or secondary amino group —NR₅R₆, when $R_5$ and $R_6$ are as before, to give a compound of the formula

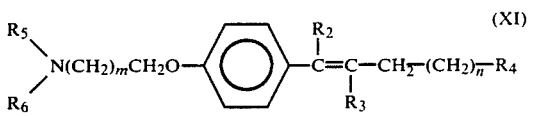
(XI)

Still another process for the preparation of compounds (I) wherein $R_4$ is hydroxy and n is 0, comprises reacting a ketone of the formula

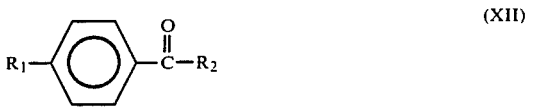
(XII)

wherein $R_1$ and $R_2$ are defined as before, with an ester, e.g. ethyl ester, of an α-bromocarboxylic acid of the formula R₃CHBrCOOC₂H₅, wherein $R_3$ is as before, in the presence of activated zinc in dry solvent, for example in ether-benzene solution, which gives a hydroxyester of the formula

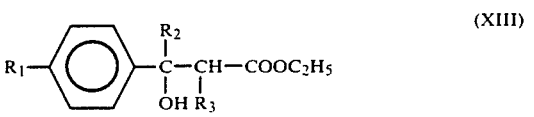
(XIII)

wherein $R_1$, $R_2$ and $R_3$ are as before. The esters of the formula (XIII), where $R_1$ is a benzyloxy radical can be catalytically hydrogenated to corresponding phenolic hydroxyesters (XIII), wherein $R_1$ is hydroxy.

The compounds of the formula (XIII) can be dehydrated to give unsaturated esters of the formula

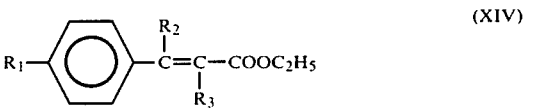
(XIV)

wherein $R_1$, $R_2$ and $R_3$ are as before. The unsaturated ester (XIV) can be reduced in one step e.g. with $LiAlH_4$, or for example via the corresponding unsaturated carboxylic acid to give an unsaturated alcohol of the formula

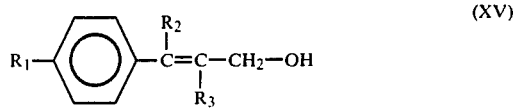
(XV)

wherein $R_1$, $R_2$ and $R_3$ are as above.

Compounds of the formula (I) wherein $R_4$ is hydroxy and n is 1 to 3 can be obtained by first replacing the hydroxyl group in the compound (XV) by a halogen atom and then preparing the Grignard reagent of the formula

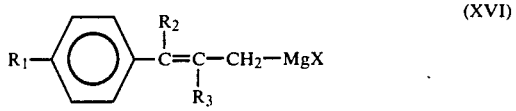
(XVI)

wherein $R_1$, $R_2$ and $R_3$ are as before and X is halogen, e.g. bromine. This reagent (XVI) can further be reacted with formaldehyde, ethylene oxide or trimethylene oxide to give an unsaturated alcohol of the formula

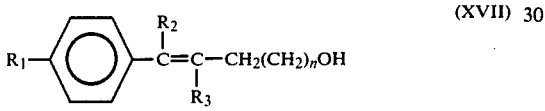
(XVII)

wherein $R_1$, $R_2$ and $R_3$ are as before and n is 1 to 3.

Still another possibility to prepare the compounds of the formula (I) comprises reacting a nitrile of the formula

(XVIII)

wherein $R_1$ and $R_2$ are as before with an organometallic compound of the formula $R_3MgX$ or $R_3Li$, where $R_3$ is as before to give a ketone of the formula

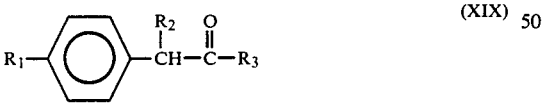
(XIX)

wherein $R_1$, $R_2$ and $R_3$ are as defined before.

The ketone of the formula (XIX) is reacted with an organometallic compound of the formula $R_4(CH_2)_nCH_2MgX$ or $R_4(CH_2)_nCH_2Li$, where $R_4$ is as before or benzyloxy or mixed acetal to produce a hydroxy compound of the formula

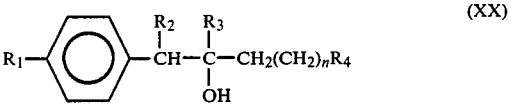
(XX)

wherein $R_1$, $R_2$, $R_3$, $R_4$ and n are as above. Compounds of the formula (XX) can be dehydrated to give compounds of the formula (I). The possible protecting group in $R_4$ can be removed simultaneously with the dehydration process or before it.

Still another way to produce compounds (I) where $R_2$ is an aromatic group comprises reacting a diphenylmethyllithium of the formula

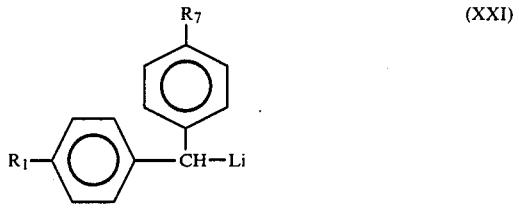
(XXI)

wherein $R_1$ and $R_7$ are as defined before or mixed acetal, with an aliphatic ketone of the formula

(XXII)

wherein $R_3$, $R_4$ and n are as before, which produces the hydroxycompound of the formula

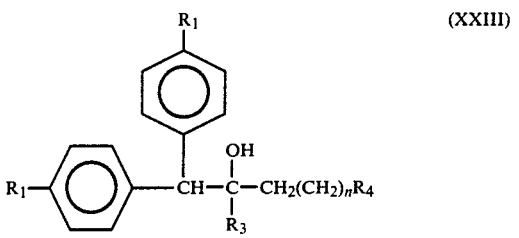
(XXIII)

where $R_1$, $R_3$, $R_4$, $R_7$ and n are as above. Dehydration and removal of the possible protecting groups in $R_1$ or in $R_7$ give a diphenylalkene of the formula

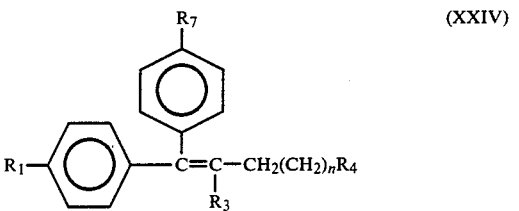
(XXIV)

wherein $R_1$, $R_3$, $R_4$, $R_7$ and n are as defined before.

Further, compounds (I), where $R_1$ is OH can be prepared by dealkylation of the corresponding alkoxy compounds for example with boron tribromide, pyridine hydrochloride or hydrogen bromide in acetic acid.

Compounds of formula (II) can be prepared by catalytic hydrogenation of the corresponding compounds of formula (I).

Further, the compounds of formula (II) can be prepared in several ways using the intermediates from the preparation of compounds of the formula (I) as starting materials. For example, compounds of the formula

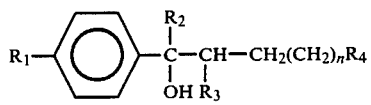

wherein $R_1$, $R_2$, $R_3$, $R_4$ and n are as defined before, can be hydrogenated in an acidic medium to give compounds of the formula (II). Further, hydroxyesters of the formula (XIII) can be similarly hydrogenated to the corresponding saturated esters of the formula

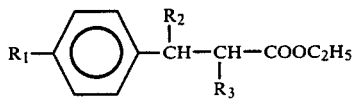

wherein $R_1$, $R_2$ and $R_3$ are as before. The synthesis can be continued according to the scheme already disclosed for the corresponding unsaturated esters (XIV).

Also, O-alkylation of the saturated phenolic compounds of the formula

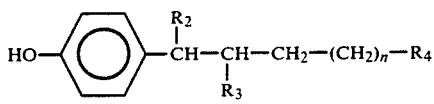

can be performed in the same manner as described for the corresponding unsaturated phenols (VIII).

As stated herein above, the compounds of the general formula (I) and (II) and their non-toxic, pharmaceutically acceptable salts and esters exhibit valuable pharmacological properties as estrogenic, anti-estrogenic, progestanic and anti-tumour activity.

Administration of isomeric compounds of formula (I) and (II), their non-toxic, pharmaceutically acceptable salts or esters or mixtures thereof may be achieved parenterally, intravenously or orally. Typically, an effective amount of the derivative is combined with a suitable pharmaceutical carrier. As used herein, the term "effective amount" encompasses those amounts which yield the desired activity without causing adverse sideeffects. The precise amount employed in a particular situation is dependent upon numerous factors such as route of administration, type of mammal, condition for which the derivative is administered, etc,. and of course the structure of the derivative.

The pharmaceutical carriers which are typically employed with the derivatives of the present invention may be solid or liquid and are generally selected with the planned manner of administration in mind. Thus, for example, solid carriers include lactose, sucrose, gelatin and agar, while liquid carriers include water, syrup, peanut oil and olive oil. Other suitable carriers are well-known to those skilled in the art of pharmaceutical formulations. The combination of the derivative and the carrier may be fashioned into numerous acceptable forms, such as tablets, capsules, suppositories, solutions, emulsions, and powders.

The affinity to estrogen receptors was determined by the ability of the molecules to compete with $^3$H-labelled 17-$\beta$-estradiol in rat uterus cytosol preparation. After incubation, receptor-bound and receptor-unbound ligands were separated by a known dextrancharcoal method. (Korenman, S. G.: "Comparative binding affinity of estrogens and its relation to estrogenic potency". Steroids 13: 163–177, 1969).

The estrogen-antiestrogen (progesterone-antiprogesterone) effect in vivo was determined as follows:

The estrogenic properties of the molecules were determined by administering the molecules, suspended in sesam oil, subcutaneously to 21 days old immature mice on three consecutive days. The mice were killed on the fourth day and the uterus was weighed. Estradiol (positive control) increases the weight of the uterus. The weight correlates with the estrogenic effect of the molecules.

The antiestrogenic effects of the molecules were determined in a similar manner in immature mice. In this case, the ability of the molecules to inhibit estrogen-induced uterus weight increase was investigated, too.

The (anti)progestanic effects were studied in a similar manners as the estrogenic ones. Medroxyprogesterone acetate, which decreases uterus weight, was used as reference.

The anti-tumour effect was studied in vitro as follows:

The growth of MCF-7 cell line (human mammary adenocarcinoma, known to be estrogen-dependent) was evaluated in the presence or absence of estradiol, medroxyprogesterone acetate or the molecules to be investigated. Combinations of molecule plus estradiol and molecule plus medroxyprogesterone were also studied. The amount of living cells after 4 h, 24 h and 48 h incubations were determined by bioluminescence assay (intracellular ATP determination).

The anti-tumour effect was investigated in vivo against DMBA-induced rat mammary adenocarcinomas and transplantable mammary adenocarcinoma according to the following methods:

Mammary adenocarcinomas were induced by DMBA in 35–40 days old female rats. Treatment with the molecules to be investigated was started after palpable tumours had appeared. Tumour size and numbers of tumours were evaluated twice a week. Tumour sizes in the control group, treated with solvent, were compared with the test groups.

Transplantable rat mammary adenocarcinoma was developed by inoculating pieces of DMBA-induced carcinomas subcutaneously to healthy mature female rats. A tumor which expressed malignant growth was selected for further transplantations.

The compounds of the invention possessed good affinities to estrogen receptors as measured by dextran-charcoal method. The results in table 1 are shown as follows:

| affinity | concentration of compound where 50% competition (inhibition) with $^3$H—estradiol occurred |
|---|---|
| + + + | $10^{-6}$M (inhibition)-$10^{-7}$M (weak affinity) |
| + + | $10^{-5}$M (inhibition)-$10^{-6}$M (weak affinity) |
| + | $10^{-4}$M (inhibition)-$10^{-5}$M (weak affinity) |
| ± | $10^{-4}$M no clear inhibition |

TABLE 1

Examples of estrogen receptor affinities of certain compounds of the invention.

| No. | Investigated compound Name | Affinity |
|---|---|---|
| 1. | (E)—2-cyclopentyl-1-(p-hydroxyphenyl)-1-phenyl-1-butene. | + + + |
| 2. | (Z)—2-cyclopentyl-1-(p-(N,N—dimethyl-2- | + +(+) |

TABLE 1-continued

Examples of estrogen receptor affinities of certain compounds of the invention.

| No. | Investigated compound Name | Affinity |
|---|---|---|
|  | amino-ethoxy)phenyl)-1-phenyl-1-butene, hydrochloride |  |
| 3. | (Z)—2-cyclopentyl-1-(p-hydroxyphenyl)-1-phenyl-1-butene | ++(+) |
| 4. | 2-cyclopentyl-1-(p-hydroxyphenyl)-1-phenyl-butane, mixt. of erythro and threo diastereomers | +++ |
| 5. | 2-cyclopentyl-1-(p-hydroxyphenyl)-1-phenyl-butane, erythro | +++ |
| 6. | 2-cyclopentyl-1-(p-hydroxyphenyl)-1-phenyl-butane, threo | +++ |
| 7. | 2-cyclopentyl-1-[p-(N,N—dimethyl-2-aminoethoxy)-phenyl]-1-(p-hydroxyphenyl)-1-butene, (E) + (Z) mixt. | +++ |
| 8. | (Z)—2-cyclopentyl-1-[p-(N,N—diethyl-2-aminoethoxy)phenyl]-1-phenyl-1-butene, citrate | +++ |
| 9. | 3-cyclopentyl-4-(p-hydroxyphenyl)-hexane | +++ |
| 10. | (Z)—2-cyclopentyl-1-[p-(N—methyl-2-aminoethoxy)-phenyl]-1-phenyl-1-butene, hydrochloride | + |
| 11. | 2-cyclopentyl-1-[p-(N,N—dimethyl-2-aminoethoxy)-phenyl]-1-(p-methoxyphenyl)-1-butene, mixt. of (E) and (Z)—isomers | + |
| 12. | 2-ethyl-3-(p-hydroxyphenyl)-1-pentanol | + |

Compounds of the invention could be characterized as ones which could be either estrogenic or antiestrogenic or both and besides could have a inhibitory or synergistic effect with medroxyprogesterone.

The estrogenic effect of compounds of the invention as measured by their ability to increase the weight of immature mouse uterus was usually far less than that of oestradiol, the positive control. With the compounds 1, 2, 7 and 8 the effect was dose dependent i.e. increased with increasing dose. At the dose of 0.5 mg/kg the oestrogenic effect of compound 1, 7 and 8 were respectively 20%, 75% and 83% less and at the dose of 5 mg/kg the oestrogenic effect of compound 2 was 60% less than that of oestradiol 0.05 mg/kg. Compounds 5 and 6 did not possess any estrogenic effects of their own.

Most of the compounds possessed antioestrogenic effect as measured by their ability to inhibit oestradiol induced weight increase in immature mouse uterus. The compound 1 at a dose of 0.5 mg/kg caused a 50% inhibition of oestradiol induced effect on mouse uterus. Compounds 2, 7 and 8 caused at the dose of 5 mg/kg a 50%, 48% and 30% inhibition respectively. Compounds 5 and 6 were not antiestrogenic.

The progestanic and antiprogestanic effects of compounds were measured as described earlier. The compound No. 2 reduced the weight of mouse uterus by 49% compared to control while medroxyprogesterone acetate gave 40% reduction. Given together with medroxyprogesterone acetate it had no antiprogestanic effects but a synergistic effect could be seen. Compounds 5 and 6 did not possess progestanic effects and a slight inhibition of medroxyprogesterone acetate produced effect was seen.

The reduction in mouse uterus weight caused by compound No. 11 2-cyclopentyl-1-[p-(N,N-dimethyl-2-aminoethoxy)phenyl]-1-(p-methoxyphenyl)-1-butene (mixture of (E) and (Z) isomers), could be considered to be purely due to its progestanic effect. Given alone it caused a 20% reduction at a dose of 0.5 mg/kg and together with medroxyprogesterone acetate a 67% reduction compared to the 40% caused by medroxyprogesterone acetate alone. Compound 7 did not posses any progestanic effects of its own and a clear dose dependant antiprogestanic effect was achieved. The effect caused by compound 8 alone at the lowest dose 0.05 mg/kg studied could be considered to be a progestanic one and a 12% decrease in uterus weight was achieved. With increased doses, however, the estrogenic effect became evident. Given together with medroxyprogesterone acetate neither synergism nor inhibition of medroxyprogesterone acetate was seen and a 16% decrease in the wight of mouse uterus was seen compared with the 20% decrease caused by medroxyprogesterone acetate alone. With higher doses an antiprogestanic effect was achieved.

In Table 2 a summary of the oestrogenic/antioestrogenic and progestanic/antiprogestanic effect of some of the compounds can be seen. The percentages refer to increase/reduction in mice uterus weights.

The antitumour effects of the compounds had been tested in vitro against MCF-7 human mammary adenocarcinoma cell line and in vivo against DMBA-induced rat mammary adenocarcinomas and transplantable mammary adenocarcinoma.

TABLE 2

Doses of compounds 0.5 mg/kg unless otherwise written.

| Given | Compound no | | | | | |
|---|---|---|---|---|---|---|
|  | 2 | 11 | 5 | 6 | 7 | 8 |
| alone | progestanic and oestrogenic effect 49% reduction | progestanic 20% reduction | neither oestrogenic nor progestanic | neither oestrogenic nor progestanic | oestrogenic | slightly oestrogenic |
| with oestradiol 0.05 mg/kg | antioestrogenic 36% reduction | neither synergism nor inhibition | neither synergism nor inhibition | neither synergism nor inhibition | antioestrogenic 48% reduction (5 mg/kg) | antiestrogenic 32% reduction (5 mg/kg) |
| with medroxyprogesterone acetate 0.06 mg/kg | synergistic effect 61% reduction | synergistic effect 67% reduction | slight inhibition | slight inhibition | clear inhibition | neither synergism nor inhibition 16% reduction |

In table 3 the antitumour effects of certain compounds can be seen. The results in it are shown as follows:

| effect | $IC_{50}$ = concentration of compound where 50% inhibition of cell growth could be seen |
|---|---|
| +++ | $10^{-6} - 5 \times 10^{-6}$ M |
| ++ | $5 \times 10^{-6} - 10^{-5}$ M |
| + | $10^{-5} - 5 \times 10^{-5}$ M |
| − | $5 \times 10^{-5}$ M |

TABLE 3

The antitumour effects of certain compounds of the invention.

| Investigated compound | Antitumour effect |
| --- | --- |
| 1 | +++ |
| 2 | ++ |
| 3 | +++ |
| 4 | +++ |
| 5 | +++ |
| 6 | +++ |
| 7 | +++ |
| 8 | +++ |
| 9 | ++(+) |
| 10 | ++ |
| 11 | ++(+) |

The antitumour effect in vivo against DMBA-induced mammary carcinomas was investigated as described earlier. At the dose of 10 mg/kg of compound 1 the growth of the tumours was slowed to an extent that the size of the tumours decreased 75% compared to the control and the number of the tumours was decreasing. Compound 2 at the dose of 7.5 mg/kg caused a 63% decrease in the size of tumours compared to the control.

The effects of compounds mentioned earlier against transplantable rat mammary adenocarcinoma can be seen in table 4.

TABLE 4

Effect of certain compounds on transplantable rat mammary adenocarcinoma

| Investigated compound | Dose mg/kg | | | | |
| --- | --- | --- | --- | --- | --- |
| | 1.0 | 5.0 | 10.0 | 20.0 | 40.0 |
| 1. | 80 | 77 | 58 | 64 | 40 |
| 2. | 82 | 87 | 69 | | |
| 11. | 87 | 87 | 50 | | |

The figures in table 4 refer to relative sizes compared to controls which is 100.

Acute toxicity, $LD_{50}$ p.o. in mice, varies from 1200 to 2000 mg/kg for the compounds tested. The clinical dosage ranges for oral administration vary from 10 to 100 mg per day and adult person.

The $^1H$ NMR spectra were measured in $CDCl_3$ on a Perkin-Elmer R 24A or a Bruker WP 80 DS instrument using TMS as internal reference (Chemical shifts in δ, ppm). The letters s, d, t and m are used to indicate a singlet, doublet, triplet or multiplet, respectively. In the same connection, the number of hydrogen atoms is also stated. The presented $^{13}C$-NMR-spectra were determined with a Bruker WP 80 DS.

EXAMPLE 1

α-cyclopentyl-p-methoxybutyrophenone

α-Cyclopentyl-p-methoxyacetophenone (13.0 g, 0.06 mol) was added slowly in dry DME (DME=Dimethoxyethane) to the suspension of NaH (8 g, 55–60% dispersion, 0.018 mmol) in dry DME under $N_2$ atmosphere at room temperature. The suspension was stirred over night. Ethyl iodide (27.7 g, 0.18 mmol) was added and stirring continued for another two hours. Ice water was added cautiously and the water layer extracted with toluene. The organic layer was washed with water, dried and evaporated to give 12.7 g (0.0052 mol, 86%) of the product.

$^1H$-NMR: 0.80 (t, 3H), 0.9–2.5 (m, 11H), 3.22 (m, 1H), 3.85 (s, 3H), 6.94 (d, 2H), 7.97 (d, 2H).

$^{13}C$-NMR: 11.93 q, 24.82 t, 24.94 t, 25.07 t, 30.73 t, 31.33 t, 43.02 d, 52.46 d, 55.37 q, 113.70 d, 130.41 d, 131.87 s, 163.29 s, 203.40 s.

EXAMPLE 2

α-Cyclopentyl-p-hydroxybutyrophenone

The mixture of 4.9 g (0.02 mol) of α-cyclopentyl-p-methoxy butyrophenone, 8.0 g (0.06 mol) of aluminium trichloride and 60 ml of benzene was refluxed for 3 hours. Dilute hydrochloric acid was added, the layers separated and the organic layer washed with water. The product was extracted with 2M sodium hydroxide. The alkaline solution was made acidic. The product was extracted with methylene chloride, dried and the solvent evaporated. The residue 4.1 g (0.018 mol, 88%) was crystallized from petroleum ether. Mp. 75°–78° C.

$^1H$-NMR: 0.81 (t, 3H), 0.9–2.4 (m, 11H), 3.25 (m, 1H), 6.98 (d, 2H).

$^{13}C$-NMR: 11.99 q, 24.79 t, 25.07 t, 30.88 t, 31.39 t, 43.17 d, 52.70 d, 115.67 d, 130.87 s, 131.08 d, 161.78 s, 205.91 s.

EXAMPLE 3

2-cyclopentyl-1-(p-hydroxyphenyl)-1-phenyl-1-butanol

A Grignard reagent was prepared from 1.8 g (0.076 mol) magnesium turnings and 11.7 g (0.075 mol) of bromobenzene in dry THF. 5.75 g (0.025 mol) of α-cyclopentyl-p-hydroxybutyrophenone in dry THF were added to the reagent and after that the mixture was refluxed for 2 hours.

A saturated ammonium chloride solution was added. The product was extracted with methylenechloride, dried and evaporated to give 7.5 g (0.024 mol, 96%) of the product. The product was used for the following step without further purification. The product was an erythro-threo-mixture, containing predominantly the threo diastereomer.

$^1H$-NMR: 0.70 and 0.75 (2t, 3H), 1–2.2 (m, 12H), 2.55 (m, 1H), 6.73 (d, 2H), 7.0–7.75 (m, 7H).

Examples 4 and 5, 4-cyclopentyl-3-(p-methoxyphenyl)-3-hexanol and 4-cyclopentyl-3-(p-hydroxyphenyl)-3-hexanol were prepared according to the procedure of the example 3 by using α-cyclopentyl-p-methoxybutyro-phenone or α-cyclopentyl-p-hydroxybutyrophenone, respectively and ethylbromide as starting materials.

EXAMPLE 4

4-cyclopentyl-3-(p-methoxyphenyl)-3-hexanol $^1H$ NMR: 0.62 (t, 3H), 1.07 (t,3H), 0.8–2.2 (m, 15H), 3.79 (s, 3H), 6.84 (d, 2H), 7.27 (d, 2H).

EXAMPLE 5

4-cyclopentyl-3-(p-hydroxyphenyl)-3-hexanol $^1H$ NMR: 0.64 (t, 3H), 0.97 (t, 3H), 0.8–2.2 (m, 15H), 6.80 (d, 2H), 7.20 (d, 2H).

EXAMPLE 6

3-cyclopentyl-4-(p-methoxyphenyl)hexane 1,1 g (4 mmol) of 4-cyclopentyl-3-(p-methoxyphenyl)-3-hexanol was hydrogenated in an acidic medium for instance in acetic acid in the presence of some drops of methanesulfonic acid by using 10% Pd-C as a catalyst to yield 0.9 g (86%) of the oily product as a mixture of threo and erythro isomers.

$^1H$ NMR: 0.6–1.0 (4t, 6H), 1.0–2.0 (m, 14H), 2.50 (m, 1H), 3.78 (s, 3H), 6.80 (d, 2H), 7.06 and 7.08 (2d, 2H).

EXAMPLE 7

3-cyclopentyl-4-(p-hydroxyphenyl)hexane was prepared from 4-cyclopentyl-3-(p-hydroxyphenyl)-3-hexanol by catalytical hydrogenation in an acidic medium.

$^1$H NMR: 0.6–1.0 (4t, 6H), 1.0–2.0 (m, 14H), 2.50 (m, 1H), 5.14 (s, 1H), 6.74 (d, 2H), 7.01 and 7.03 (2d, 2H).

EXAMPLE 8

2-cyclopentyl-1-(p-methoxyphenyl)-1-phenyl-1-butanol was prepared according to the procedure of the example 3 by using α-cyclopentyl-p-methoxybutyrophenone and bromobenzene as starting materials.

$^1$H-NMR: 0.70 and 0.75 (2t, 3H), 1.0–1.3 (complex m, 12H), 2.56 (m, 1H), 3.70 (s, 3H), 6.79 (d, 2H), 7.0–7.7 (complex, 7H).

$^{13}$C-NMR: 15.53 q, 19.74 t, 24.40 t, 25.82 t, 27.70 t, 33.36 t, 40.81 d, 50.19 d, 55.13 q, 82.19 s, 113.46 d, 125.60 d, 125.96 d, 126.81 d, 127.81 d, 139.95 s, 147.43 s, 157.93 s.

EXAMPLE 9

2-cyclopentyl-1-[p-(N,N-dimethyl-2-aminoethoxy)-phenyl]-1-(p-methoxyphenyl)-1-butanol was prepared according to the procedure of the example 3 by using α-cyclopentyl-p-methoxybutyrophenone and p-(N,N-dimethyl-2-aminoethoxy)bromobenzene as starting materials.

The product was used as the starting material for the preparation of 2-cyclopentyl-1-[p-(N,N-dimethyl-2-aminoethoxy)phenyl]-1-p-methoxyphenyl-1-butene.

EXAMPLE 10

2-cyclopentyl-1-(p-hydroxyphenyl)-1-phenyl-1-butene 4.7 g (0.015 mol) of 2-cyclopentyl-1-(p-hydroxyphenyl)-1-phenylbutanol was dissolved in 100 ml of methylene chloride, 4 ml of trifluoroacetic acid was added dropwise. The mixture was stirred in room temperature for 1 hour, after which it was evaporated to dryness. The product was dissolved in toluene and washed with water. Dilute sodium hydroxide was added and the formed sodium salt of the product (3,5 g) filtered off. The sodium salt was suspended in toluene and dilute hydrochloric acid was added to liberate the product from its salt. The toluene solution was washed with water, dried and evaporated. The product was fractionally crystallized very carefully from petroleum ether to give first the E-isomer and then the Z-isomer. Melting point for the Z-isomer was 111.5–112.5 and for the E-isomer 109°–109.5° C.

E-isomer:

$^1$H-NMR: 0.87 (t, 3H), 1.2–1.9 (m, 8H), 2.09 (q, 2H), 2.5–3.0 (m, 1H), 4.7 (s, 1H), 6.70 (d, 2H), 7.05 (d, 2H), 7.0–7.5 (m, 5H).

$^{13}$C-NMR: 15.23 q, 21.52 t, 25.64 t, 31.64 t, 44.14 d, 114.91 d, 125.78 d, 127.92 d, 128.99 d, 130.38 d, 136.59 s, 138.04 s, 142.86 s, 144.19 s, 153.57 s, propionate, mp. 65.5°–67.5° C. benzoate mp. 134°–136° C.

Z-isomer:

$^1$H-NMR: 0.85 (t, 3H), 1.2–1.9 (m, 8H), 2.07 (q, 2H), 2.5–3.0 (m, 1H), 4.7 (s, 1H), 6.70 (d, 2H), 7.02 (d, 2H), 7.0–7.5 (m, 5H).

$^{13}$C-NMR: 15.26 q, 21.52 t, 25.64 t, 31.67 t, 44.05 d, 114.89 d, 125.81 d, 127.96 d, 129.11 d, 130.26 d, 136.62 s, 138.07 s, 142.73 s, 144.13 s, 153.60 s.

In the examples 11 and 12 the procedure of the example 10 was repeated except that in place of 2-cyclopentyl-1-(p-hydroxyphenyl)-1-phenylbutanol the corresponding butanols from the examples 8 and 9 were used.

EXAMPLE 11

2-cyclopentyl-1-(p-methoxyphenyl)-1-phenyl-1-butene

The Z-isomer could be crystallized 92% pure from methanol M.p. 78°–84° C.

Pure E- and Z-isomers were prepared from the corresponding phenol isomers (from the example 10) by methylation with dimethyl sulfate in ethanol solution made alkaline with sodium hydroxide using tetrabutylammonium hydrogensulfate as a catalyst. Melting point for the Z-isomer was 88°–90° C. and for the E-isomer 45°–47° C.

E-isomer:

$^1$H-NMR: 0.88 (t, 3H), 1.1–1.8 (compl., 8H), 2.10 (q, 2H), 2.78 (m, 1H), 3.73 (s, 3H), 6.78 (d, 2H), 7.11 (d, 2H), 7.0–7.5 (compl., 5H).

$^{13}$C-NMR: 15.28 q, 21.61 t, 25.66 t, 31.67 t, 44.17 d, 55.10 q, 113.46 d, 125.75 d, 127.90 d, 128.99 d, 130.17 d, 136.35 d, 138.22 s, 142.70 s, 144.22 s, 157.78 s.

Z-isomer:

$^1$H-NMR: 0.86 (t, 3H), 1.1–1.8 (compl., 8H), 2.07 (q, 2H), 2.78 (m, 1H), 3.73 (s, 3H), 6.78 (d, 2H), 7.09 (d, 2), 7.0–7.5 (compl., 5H).

$^{13}$C-NMR: 12.26 q, 21.61 t, 25.64 t, 31.67 t, 44.08 d, 55.10 q, 113.4 d, 125.75 d, 127.96 d, 1269.11 d, 130.05 d, 136.35 s, 138.22 s, 142.58 s, 144.19 s, 157.78 s.

EXAMPLE 12

2-cyclopentyl-1-[p-(N,N-dimethyl-2-aminoethoxy)-phenyl]-1-p-methoxyphenyl-1-butene (mixture of E- and Z-isomers).

$^1$H-NMR: 0.86 (t, 3H), 1.2–1.8 (compl., 8H), 2.08 (q, 2H), 2.32 (s, 6H), 2.70 (t, 2H) under which (m, 1H), 3.76 (s, 3H), 4.03 (t, 2H), 6.79 (d, 4H), 7.04 and 7.06 (2d, 4H).

$^{13}$C-NMR: 15.26 q, 21.58 t, 25.64 t, 31.67 t, 44.14 d, 45.89 q, 55.10 q, 58.40 t, 65,96 t, 113.37 d, 113.98 and 114.07 d, 130.02 and 130.111 d, 136.71 and 136.77 s, 137.68 s, 142.49 s, 156.96 s, 157.66 s.

EXAMPLE 13

2-cyclopentyl-1-[p-(N,N-dimethyl-2-aminoethoxy)-phenyl]-1-(p-hydroxyphenyl)-1-butene (mixture of E- and Z-isomers).

2-cyclopentyl-1-[p-(N,N-dimethyl-2-aminoethoxy)-phenyl]-1-(p-hydroxyphenyl)-1-butanol, which was prepared from α-cyclopentyl-p-hydroxybutyrophenone and p-(N,N-dimethyl-2-aminoethoxy) bromobenzene according to the procedure of example 3, was dehydrated in ethanol in the presence of hydrochloric acid. The product was recrystallized from n-hexane, mp. 112°–120° C. and was found to be an 1:1 mixture of E- and Z-isomers.

$^1$H-NMR: 0.843 and 0.853 (t. 3H), 1.1–1.8, (m, 8H), 2.079 (q, 2H), 2.383 (s, 6H), 2.779 (t, 2H), 4.038 (t, 2H), 6.68 (d, 4H), 6.8–7.1 (m, 4H).

$^{13}$C-NMR: 15.29 q, 21.58 q, 25.64 t, 31.67 t, 44.14 d, 45.41 q, 58.09 t, 65.15 t, 113.95 d, 115.16 and 115.22 d, 130.14 and 130.23 d, 135.74 s, 137.10 s, 142.25 s, 154.84 s, 156.60 s.

EXAMPLE 14

2-cyclopentyl-1-[p-(N,N-dimethyl-2-aminoethoxy)-phenyl]-1-phenyl-1-butene 1.2 g (4 mmol) of pure (E)- or (Z)-isomer of 2-cyclopentyl-1-(p-hydroxyphenyl)-1-phenyl-1-butene, 0.880 g (6 mmol) of 2-chloro-1-dimethylaminoethane hydrochloride, 48 mg of TEBAC, 0.32 g (8 mmol) of powdered sodium hydroxide and 6 ml of dry toluene was refluxed for 7 hours, additional 0.44 g of 2-chloro-1-dimethylaminoethane hydrochloride and 0.16 g of sodium hydroxide were added and refluxing was continued for another 6 hours. Water was added and the toluene layer was washed with water, dried and evaporated to give 0.9 g (2.4 mmol, 62%) of the amine product.

Z-isomer, hydrochloride mp. 212°–214° C.

$^1$H NMR (free base): 0.855 (t, 3H), 1.1–1.8 (m, 8H), 2.069 (q, 2H), 2.302 (s, 6H), 2.68 (t+m, together 3H), 4.01 (t, 2H), 6.79 (d, 2H), 7.06 (d, 2H), 7.0–7.5 (m, 5H).

$^{13}$C NMR: 15.26 q, 21.71 t, 25.70 t, 31.73 t, 44.14 d, 45.92 q, 58.49 t, 66.33 t, 114.22 d, 125.78 d, 127.96 d, 129.14 d, 130.05 d, 136.56 s, 138.44 s, 142.70 s, 144.28 s, 157.24 s.

E-isomer, hydrochloride mp. 182°–185° C.

$^1$H NMR (free base): 0.870 (t, 3H), 1.1–1.8 (m, 8H), 2.093 (q, 2H), 2.316 (s, 6H), 2.69 (t+m, together 3H), 4.02 (t, 2H), 6.81 (d, 2H), 7.03 (d, 2H), 7.0–7.5 (m, 5H).

EXAMPLE 15

(Z)-2-cyclopentyl-1-[p-(N,N-diethyl-2-aminoethoxy)phenyl]-1-phenyl-1-butene.

The compound was prepared according to the procedure of example 14 by using 2-chloro-1-diethylaminoethane hydrochloride as the amine component. Citrate mp. 142°–144° C.

$^1$H-NMR (free base): 0.856 (t, 3H), 1.048 (t, 6H), 1.3–1.8 (m, 8H), 2.070 (q, 2H), 2.618 (q, 4H), 2.848 (t, 2H), under which (m, 1H) 4.005 (t, 2H), 6.786 (d, 2H), 7.05 (d, 2H), 7.1–7.3 (5H).

$^{13}$C-NMR: 12.02 q, 15.26 q, 21.61 t, 25.64 t, 31.67 t, 44.08 d, 47.92 t, 51.98 t, 66.60 t, 114.01 d, 125.75 d, 127.93 d, 129.11 d, 130.02 d, 136.35 s, 138.28 s, 142.55 s, 144.22 s, 147.14 s.

EXAMPLE 16

(Z)-2-cyclopentyl-1-[p-(N,-methyl-2-aminoethoxy)-phenyl]-1-phenyl-1-butene.

2.92 g (mmol) of (Z)-2-cyclopentyl-1-(p-hydroxyphenyl)-1-phenyl-1-butene, 2.1 g of potassium carbonate and 9.4 g (50 mmol) of 1,2-dibromoethane were refluxed in 25 ml of 2-butanone for two days. The precipitate was filtered off. Ether was added to the filtrate and the solution washed with 2M sodium hydroxide to remove the unreacted starting material. After drying over sodium sulfate the ether was evaporated and the residue recrystallized from methanol. The yield of the 2-cyclopentyl-1-[p-(2-bromoethoxy)phenyl]-1-phenyl-1-butene was 1.87 g (47%).

$^1$H-NMR: 0.856 (t, 3H), 1.1–1.8 (m, 8H), 2.069 (q, 2H), 2.75 (m, 1H), 3.591 (t, 2H), 4.239 (t, 2H), 6.84 (d, 2H), 7.02 (d, 2H), 7–7.3 (m, 5H).

400 mg (1 mmol) of the above bromo-compound was heated in 16 ml of 33% methylamine-ethanol solution in an autoclave at 100° C. for six hours. The solvent was evaporated and the amine was liberated from its hydrobromide salt by toluene-10% sodium carbonate extraction. The organic layer was washed with water, dried and the toluene evaporated. The yield was 320 mg (91.7%). Melting point of the hydrochloride salt was 192°–194° C.

$^1$H-NMR (free base): 0.856 (t, 3H), 1.0–2.0 (m, 8H), 2.070 (q, 2H), 2.488 (s, 3H), 2.944 (t, 2H) under which at 2.8 (m, 1H), 4.041 (t, 2H), 6.836 (d. 2H), 7.011 (d, 2H), 7.0–7.4 (m, 5H).

$^{13}$C-NMR: 15.26 q, 21.61 t, 25.67 t, 31.69 t, 36.21 q, 44.08 d, 50.89 t, 66.96 t, 114.07 d, 125.78 d, 127.96 d, 129.12 d, 130.08 d, 136.59 s, 138.22 s, 142.64 s, 144.16 s, 157.08 s.

EXAMPLE 17

Ethyl 2-ethyl-3-hydroxy-3-(p-methoxyphenyl)-3-phenylpropionate

The mixture containing 14.6 g (0.069 mol) of p-methoxybenzophenone and 14.8 g (0.076 mol) of ethyl α-bromobutyrate in 20 ml of dry benzene and 20 ml of dry ether was added dropwise to the warm stirred suspension of 4.96 g (0.076 mol) of activated zinc powder in 10 ml of dry benzene and 10 ml of dry ether. The mixture was refluxed for 5 hours. Ice-cold 10% sulphuric acid was added. The organic layer was washed with 5% sulphuric acid, 5% sodium carbonate and water, dried and evaporated to give 19.4 g (0.059 mol, 86%) of product, mp. 106°–115° C., which was a mixture of the erythro and threo diastereomers. The diastereomers could be enriched by crystallization from petroleum ether.

1. isomer $^1$H-NMR: 0.86 (t, 3H), 1.11 (t, 3H), 1.2–2.1 (compl, 2H), 3.42 (dd, 1H), 3.73 (s, 3H), 4.05 (q, 2H), 4.64 (s, 1H), 6.79 (d, 2H), 7.0–7.7 (compl, 7H).

2. isomer $^1$H-NMR: 0.87 (t, 3H), 1.06 (t, 3H), 1.2–2.1 (compl, 2H), 3.42 (dd, 1H), 3.73 (s, 3H), 4.01 (q, 2H), 4.63 (s, 1H), 6.80 (d, 2H), 7.0–7.7 (compl, 7H).

In the examples 18–20 the procedure of the example 17 was repeated except that in the place of p-methoxybenzophenone the corresponding phenones were used.

EXAMPLE 18

Ethyl 3-(p-benzyloxyphenyl)-2-ethyl-3-hydroxy-3-phenylpropionate, mp. 84°–90° C.

1. isomer $^1$H-NMR: 0.87 (t, 3H), 1.08 (t, 3H), 1.4–2.2 (compl, 2H), 3.41 (dd, 1H), 4.03 (q, 2H), 4.64 (s, 1H), 4.98 (s, 2H), 6.86 (d, 2H), 7.0–7.2 (compl., 12H).

2. isomer $^1$H-NMR: 0.86 (t, 3H), 1.05 (t, 3H), 1.4–2.2 (compl., 2H), 3.41 (dd, 1H), 4.01 (q, 2H), 4.64 (s, 1H), 4.98 (s, 2H), 7.0–7.2 (compl., 12H).

EXAMPLE 19

Ethyl 2-ethyl-3-hydroxy-3-(p-methoxyphenyl)pentanoate mp. 64°–70° C.

1. isomer $^1$H-NMR: 0.64 (t, 3H), 0.92 (t, 3H), 0.94 (t, 3H), 1.45–2.2 (m, 4H), 2.82 (t, 1H), 3.77 (s, 3H), 3.86 (q, 2H), 3.9 (s, 1H), 6.82 (d, 2H), 7.29 (d, 2H).

$^{13}$C-NMR: 7.63 q, 12.32 q, 13.90 q, 20.16 t, 31.97 t, 55.16 q, 56.13 d, 60.15 t, 77.10 s, 113.10 d, 126.78 d, 137.41 s, 158.26 s, 176.28 s.

2. isomer $^1$H-NMR: 0.64 (t, 3H), 0.73 (t, 3H), 1.33 (t, 3H), 1.45–2.2 (m, 4H), 2.65 (dd, 1H), 3.57 (s, 1H), 3.80 (s, 3H), 4.26 (q, 3H), 6.86 (d, 2H), 7.27 (d, 2H).

$^{13}$C-NMR: 7.72 q, 12.11 q, 14.35 q, 20.95 t, 34.87 t, 55.16 q, 57.43 d, 60.64 t, 77.10 s, 113.34 d, 126.66 d, 135.02 s, 158.11 s, 177.03 s.

EXAMPLE 20

Ethyl 3-(p-benzyloxyphenyl)-2-ethyl-3-hydroxypentanoate Mp., 62°–72° C. after crystallization from petroleum ether.

1. isomer $^1$H-NMR: 0.64 (t, 3H), 0.89 (t, 3H), 0.91 (t, 3H), 1.5–2.2 (m, 4H), 2.81 (t, 1H), 3.84 (q, 2H), 3.9 (s, 1H), 5.03 (s, 2H), 6.90 (d, 2H), 7.2–7.6 (compl, 7H).

2. isomer $^1$H-NMR: 0.63 (t, 3H), 0.73 (t, 3H), 1.32 (t, 3H), 1.5–2.2 (m, 4H), 2.65 (dd, 1H), 4.26 (q, 2H), 5.03 (s, 2H), 6.90 (d, 2H), 7.2–7.6 (compl., 7H).

EXAMPLE 21

Ethyl 2-ethyl-3-hydroxy-3-(p-hydroxyphenyl)-3-phenylpropionate 8.0 g (0.020 mol) of ethyl 3-(p-benzyloxyphenyl)-2-ethyl-3-hydroxy-3-phenylpropionate were hydrogenated in ethanol solution using palladium-charcoal as catalyst to yield 6.0 g (96%) of the product, mp. 46°–53° C.

$^1$H-NMR: 0.86 and 0.88 (2t, 3H), 1.10 and 1.05 (2t, 3H), 1.2–2.2 (complex, 2H), 3.41 (dd, 1H), 4.05 and 4.01 (2q, 2H), 4.6 (b, 1H), 5.5 (b, 1H), 6.71 (d, 2H), 7.0–7.6 (compl., 7H).

EXAMPLE 22

Ethyl 2-ethyl-3-hydroxy-3-(p-hydroxyphenyl)pentanoate

This was similarly prepared by catalythical hydrogenation of ethyl 3-(p-benzyloxyphenyl)-2-ethyl-3-hydroxypentanoate.

$^1$H-NMR: 0.64 (2t, 3H), 0.95 and 0.73 (2t, 3H from the two diastereomers), 0.95 and 1.33 (2t, 3H), 1.4–2.2 (compl., 4H), 2.85 (t) and 2.64 (dd, 1H), 3.89 and 4.16 (2q, 2H), 6.77 and 6.80 (2d, 2H), 7.22 (d, 2H).

EXAMPLE 23

Ethyl 2-ethyl-3-(p-methoxyphenyl)-3-phenylpropenoate 7.3 g (0.02 mol) of ethyl 2-ethyl-3-hydroxy-3-(p-methoxyphenyl)-3-phenylpropionate were dehydrated in 150 ml of chloroform by using trifluoroacetic acid as catalyst (see example 10) to give 6.7 g (93%) of product, which was a mixture of E- and Z-isomers.

E-isomer:

$^1$H-NMR: 0.87 (t, 3H), 1.10 (t, 3H), 2.45 (q, 2H), 3.78 (s, 3H), 3.93 (q, 2H), 6.84 (d, 2H), 7.09 (d, 2H), 7.0–7.3 (m, 5H).

Z-isomer:

$^1$H-NMR: 0.98 (t, 3H), 1.07 (t, 3H), 2.38 (q, 2H), 3.77 (s, 3H), 4.01 (q, 2H), 6.76 (d, 2H), 7.06 (d, 2H), 7.1–7.4 (m, 5H).

EXAMPLE 24

Ethyl 2-ethyl-3-(p-hydroxyphenyl)-3-phenylpropenoate was similarly (example 10) prepared by dehydration from ethyl 2-ethyl-3-hydroxy-3-(p-hydroxyphenyl)-3-phenylpropionate. The other isomer (E) could be enriched 90% pure by recrystallization from methanol. Mp. 173°–175° C.

E-isomer:

$^1$H-NMR: 0.88 (t, 3H), 1.09 (t, 3H), 2.45 (q, 2H), 3.93 (q, 2H), 6.77 (d, 2H), 7.01 (d, 2H), 7.0–7.4 (m, 5H).

Z-isomer:

$^1$H-NMR: 0.99 (t, 3H), 1.07 (t, 3H), 2.36 (q, 2H), 4.02 (q, 2H), 6.69 (d, 2H), 6.97 (d, 2H), 7.0–7.5 (m, 5H).

EXAMPLE 25

2-Ethyl-3-(p-methoxyphenyl)-3-phenyl-2-propen-1-ol 1.04 g (30 mmol) of LiAlH$_4$ were suspended in 25 ml of dry ether. 1.38 g (30 mmol) of dry ethanol in ether were cautiously added to this suspension. 16 ml of this reagent were in 2 ml portions at 1 hour intervals added to a stirred solution of 1.86 g (6 mmol) of ethyl 2-ethyl-3-(p-methoxyphenyl)-3-phenylpropenoate in 16 ml of dry ether. After the reaction was complete, ice water was added cautiously and the precipitated aluminium salts were filtered off. The water layer was extracted with ether. The combined ether solutions were dried and evaporated to give 1.24 g (4.6 mmol, 77%) of the oily product as a mixture of E- and Z-isomers.

$^1$H-NMR: 1.06 and 1.08 (2t, 3H), 1.5 (b, 1H), 2.25 and 2.30 (2q, 2H), 3.766 and 3.773 (2s, 3H), 4.21 and 4.17 (2s, 2H), 6.80 and 6.82 (2d, 2H), 7.07 (d, 2H), 7.0–7.5 (m, 5H).

EXAMPLE 26

(E)-2-ethyl-3-(p-hydroxyphenyl)-3-phenyl-2-propen-1-ol was prepared by reducing the corresponding ester from the example 24 by LiAlH$_4$ (see example 25). Mp. 112°–116° C.

$^1$H NMR: 1.07 (t, 3H), 2.0 (s, 2H), 2.30 (q, 2H), 4.17 (s, 2H), 6.73 (d, 2H), 6.99 (d, 2H), 6.8–7.5 (m, 5H).

EXAMPLE 27

Ethyl 2-ethyl-3-(p-methoxyphenyl)pentanoate 10.7 g (0.038 mol) of ethyl 2-ethyl-3-hydroxy-3-(p-methoxyphenyl)pentanoate were hydrogenated in acetic acid (88 ml) solution in the presence of methanesulfonic acid (7 drops) by using 10% Pd-C as catalyst. The catalyst was filtered off and the solvent was evaporated. The product was dissolved in methylene chloride, washed with diluted potassium carbonate and water and dried. After evaporation of the solvent 9,5 g (97%) of the product as a mixture of erythro and threo diastereomers were obtained.

$^1$H-NMR: 0.65, 0.70, 0.74, 0.89, 0.98 and 1.30 (6t, 9H, 3 methyl groups of the two diastereomers), 1.2–2.0 (compl, 4H), 2.2–2.8 (compl, 2H), 3.77 and 3.79 (2s, 3H), 3.85 and 4.20 (2q, 2H), 6.79 and 6.83 (2d, 2H), 7.06 (d, 2H).

EXAMPLE 28

2-Ethyl-3-(p-methoxyphenyl)-1-pentanol was obtained from ethyl 2-ethyl-3-(p-methoxyphenyl)pentanoate by LiAlH$_4$ reduction in dry ether.

$^1$H-NMR: 0.71, 0.73, 0.90 and 0.94 (4t, 6H), 1.1–2.0 (compl. 5H), 2.52 (m, 1H), 3.42 and 3.64 (2m, 2H), 3.79 (s, 3H), 6.82 (d, 2H), 7.08 (d, 2H).

EXAMPLE 29

2-Ethyl-3-(p-hydroxyphenyl)-1-pentanol was similarly obtained by LiAlH$_4$ reduction from ethyl 2-ethyl-3-(p-hydroxyphenyl)pentanoate as a mixture of erythro- and threodiastereomers and purified by chromatographing on silicagal to give viscous semisolid product.

$^1$H-NMR: 0.69, 0.72, 0.90 and 0.93 (4t, 3H), 1.0–2.0 (compl, 5H), 2.1–2.7 (m, 1H), 3.46 and 3.69 (2m, 2H), 6.71 (d, 2H), 6.99 (d, 2H).

EXAMPLE 30

2-cyclopentyl-1-(p-methoxyphenyl)-1-phenylbutane was prepared by catalytical hydrogenation in ethanol from (Z,E) 2-cyclopentyl-1-(p-methoxyphenyl)-1-phenyl-1-butene by using 10% Pd-C as a catalyst. The product was a mixture of threo and erythro isomers.

$^1$H NMR: 0.688 and 0.703 (2t, 3H), 1.0–2.0 (m, 11H), 2.20 (m, 1H), 3.73 (d, 1H), 6.77 (d, 2H), 7.22 (d, 2H), 7.0–7.5 (m, 5H).

EXAMPLE 31

2-cyclopentyl-1-(p-hydroxyphenyl)-1-phenylbutane was similarly prepared by catalytical hydrogenation in ethanol from 2-cyclopentyl-1-(p-hydroxyphenyl)-1-phenyl-1-butene.

$^1$H NMR: 0.681 and 0.694 (2d, 3H), 1.0–2.0 (m, 11H), 2.20 (m, 1H), 3.70 (d, 1H), 6.68 (d, 2H), 7.13 (d, 2H), 7.0–7.5 (m, 5H).

Pure erythro and threo-isomers could be obtained by hydrogenation of the pure Z- and E-isomers of the starting material respectively.

EXAMPLE 32

2-cyclopentyl-1-(p-allyloxyphenyl)-1-phenyl-1-butene 2.92 g (10 mmol) of pure E- or Z-isomer of 2-cyclopentyl-1-(p-hydroxyphenyl)-1-phenyl-1-butene in dry DME was added under nitrogen atmosphere to a stirred suspension of sodium hydride in DME (0.6 g of 50–60% dispersion from which the oil had been removed by washing with dry DME). After stirring for 30 minutes at room temperature, 1.44 g (12 mmol) of allyl bromide was added. The mixture was refluxed for 3 hours. Ice water was added. The water layer was extracted with ether and the combined organic layers washed with diluted sodium hydroxide and water and dried. After evaporation of the solvent the residue was 3.1 g. In the case of the E-isomer the semisolid product was purified by chromatography over silica gel using methylene chloride as eluent. The Z-isomer was purified by recrystallization from methanol, mp. 82°–84° C.

E-isomer:
$^1$H NMR: 0.875 (t, 3H), 1.2–1.9 (m, 8H), 2.095 (q, 2H), 2.75 (m, 1H), 4.48 (m, 2H), 5.15–5.60 (m, 2H), 5.8–6.3 (m, 1H), 6.81 (d, 2H), 7.09 (d, 2H), 7.0–7.5 (m, 5H).

Z-isomer:
$^1$H NMR: 0.855 (t, 3H), 1.2–1.9 (m, 2H), 2.060 (q, 2H), 2.75 (m, 1H), 4.48 (m, 2H), 5.15–5.60 (m, 2H), 5.80–6.30 (m, 2H), 6.80 (d, 2H), 7.06 (d, 2H), 7.0–7.3 (m, 5H).

EXAMPLE 33

2-cyclopentyl-1-[p-(2,3-epoxypropoxy)phenyl]-1-phenyl-1-butene was prepared according to the procedure of the example 32 using epichlorohydrine as the O-alkylating agent. The E-isomer was purified by chromatography over silica gel using methylene chloride as eluent.

$^1$H NMR: 0.870 (t, 3H), 1.1–1.8 (m, 8H), 2.114 (q, 2H), 2.55–3.00 (m, 3H), 3.30 (m, 1H), 3.75–4.30 (m, 2H), 6.81 (d, 2H), 7.10 (d, 2H), 7.0–7.4 (m, 5H).

The Z-isomer was recrystallized from methanol, mp. 79°–82° C.

$^1$H NMR: 0.853 (t, 3H), 1.1–1.8 (m, 8H), 2.074 (q, 2H), 2.55–2.95 (m, 3H), 3.30 (m, 1H), 3.75–4.30 (m, 2H), 6.80 (d, 2H), 7.07 (d, 2H), 7.0–7.4 (m, 5H).

EXAMPLE 34

2-cyclopentyl-1-[p-(2,3-dihydroxypropoxy)phenyl]-1-phenyl-1-butene was prepared from pure E- or Z-isomer of 2-cyclopentyl-1-(p-hydroxyphenyl)-1-phenyl-1-butene and 3-chloro-1,2-propandiol in 2-butanone using potassium carbonate as a base (see example 16). In the case of the E-isomer the semisolid product was purified by chromatography over silica gel using methylene chloride as eluent.

$^1$H NMR: 0.868 (t, 3H), 1.1–1.8 (m, 8H), 2.09 (q, 2H), 2.75 (m, 1H), 3.70 (m, 2H), 3.98 (m, 2H) under which (m, 1H), 6.81 (d, 2H), 7.10 (d, 2H), 7.0–7.4 (m, 5H).

The Z-isomer was recrystallized from petroleum ether, mp. 89°–91° C.

$^1$H NMR: 0.858 (t, 3H), 1.1–1.8 (m, 8H), 2.07 (q, 2H), 2.75 (m, 1H), 3.76 (m, 2H), 4.02 (m, 2H), under which (m, 1H), 6.79 (d, 2H), 7.07 (d, 2H), 7.0–7.4 (m, 5H).

We claim:

1. A compound of the general formula:

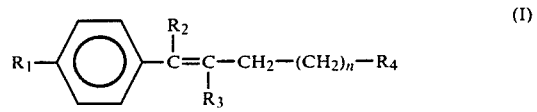

or

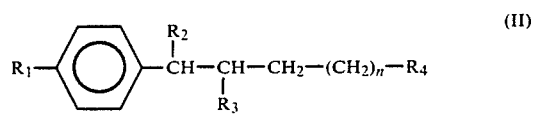

wherein $R_1$ is hydrogen, hydroxy, alkoxy of 1 to 4 carbon atoms, allyloxy, 2,3-epoxypropoxy, 2,3-dihydroxypropoxy, or $$-O-CH_2(CH_2)_m-\overset{R_5}{\underset{}{N}}-R_6$$

wherein one of $R_5$ and $R_6$ is hydrogen and the other an alkyl group of 1 to 4 carbon atoms or $R_5$ and $R_6$ are alkyl groups of 1–4 carbon atoms which may be the same or different or the $-NR_5R_6$ group stands for a nitrogen-containing 5 to 7 membered heterocyclic radical and m is 1 or 2;

$R_2$ is

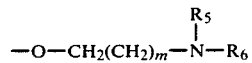

wherein
$R_7$ has the same meanings as $R_1$ except that $R_7$ and $R_1$ cannot simultaneously be the same and, when $R_1$ is a radical as aforesaid other than hydrogen, $R_2$ is an alkyl of 1 to 4 carbon atoms; $R_3$ is cyclopentyl or hydroxycyclopentyl; $R_4$ is hydrogen or hydroxy and n is 0 to 3, and its non-toxic pharmaceutically acceptable salts and esters.

2. A compound of formula (I) according to claim 1 wherein it is an (E)-isomer, (Z)-isomer or a mixture thereof.

3. A compound of formula (I) according to claims 1–2 wherein $R_2$ is

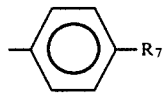

and R₇ is as defined in claim 1.

4. A compound according to claim 3 wherein R₄ is hydrogen and n is 1.

5. A compound of formula (I) according to claims 1-2 wherein R₂ is phenyl.

6. A compound according to claim 5 wherein R₄ is hydrogen and n is 1.

7. A compound of formula (II) according to claim 1 wherein R₂ is

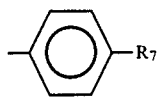

and R₇ is as defined in claim 1.

8. A compound according to claim 7 wherein R₄ is hydrogen and n=1.

9. A compound of formula (II) according to claim 1 wherein R₂ is phenyl.

10. A compound according to claim 9 wherein R₄ is hydrogen and n is 1.

11. A compound according to claim 1 which is 2-cyclopentyl-1-[p-(N,N-dimethyl-2-aminoethoxy)-phenyl]-1-(p-methoxyphenyl)-1-butene, its (E)-isomer, (Z)-isomer or a mixture thereof and its salts.

12. A compound according to claim 1 which is 2-cyclopentyl-1-(p-methoxyphenyl)-1-phenyl-1-butene and its (E)-isomer, (Z)-isomer or a mixture thereof.

13. A compound according to claim 1 which is 2-cyclopentyl-1-(p-hydroxyphenyl)-1-phenyl-1-butene and its (E)-isomer, (Z)-isomer or a mixture thereof, and its esters and salts.

14. A compound according to claim 1 which is 2-cyclopentyl-1-[p-(N,N-dimethyl-2-aminoethoxy)-phenyl]-1-phenyl-1-butene, its (E)-isomer, (Z)-isomer or a mixture thereof and its salts.

15. A compound according to claim 1 which is 2-cyclopentyl-1-(p-methoxyphenyl)-1-phenylbutane.

16. A compound according to claim 1 which is 2-cyclopentyl-1-(p-hydroxyphenyl)-1-phenylbutane and its esters and salts.

17. A compound according to claim 1 which is 3-cyclopentyl-4-(p-methoxyphenyl)hexane.

18. A compound according to claim 1 which is 3-cyclopentyl-4-(p-hydroxyphenyl)hexane and its esters and salts.

19. A compound according to claim 1 which is 2-cyclopentyl-1-[p-(N,N-dimethyl-2-aminoethoxy)-phenyl]-1-(p-hydroxyphenyl)-1-butene, its (E)-isomers, (Z)-isomer or a mixture thereof and its esters and salts.

20. A compound according to claim 1 which is 2-cyclopentyl-1-[p-(N,N-diethyl-2-aminoethoxy)phenyl]-1-phenyl-1-butene, its (E)-isomer, (Z)-isomer or a mixture thereof and its salts.

21. A compound according to claim 1 which is 2-cyclopentyl-1-[p-(N-methyl-2-aminoethoxy)phenyl]-1-phenyl-1-butene, its (E)-isomer, (Z)-isomer or a mixture thereof and its salts.

22. A compound according to claim 1 which is 2-(3-hydroxyl-1-cyclopentyl)-1-(p-methoxyphenyl)-1-phenyl-1-butene and its esters.

23. A compound according to claim 1 which is 2-(3-hydroxy-1-cyclopentyl)-1-(p-hydroxyphenyl)-1-phenyl-1-butene and its esters.

24. A compound according to claim 1 which is 2-(3-hydroxy-1-cyclopentyl)-1-[p-(N,N-dimethyl-2-aminoethoxy)phenyl]-1-phenyl-1-butene and its salts and esters.

25. A pharmaceutical composition comprising a compound as claimed in claim 1 or a non-toxic pharmaceutically acceptable salt or ester thereof and a compatible pharmaceutically acceptable carrier therefor.

26. Method for inhibiting and reducing the growth of an oestrogen dependent tumour which comprises treating such a tumour with an effective amount of a compound of the general formula

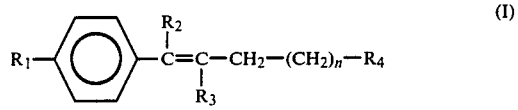

or

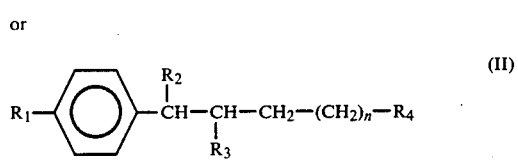

wherein R₁ is hydrogen, hydroxy, alkoxy of 1 to 4 carbon atoms, allyloxy, 2,3-epoxypropoxy, 2,3-dihydroxypropoxy, or

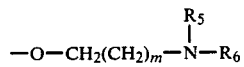

wherein one of R₅ and R₆ is hydrogen and the other an alkyl group of 1 to 4 carbon atoms or R₅ and R₆ are alkyl groups of 1–4 carbon atoms which may be the same or different or the —NR₅R₆ group stands for a nitrogen-containing 5 to 7 membered heterocyclic radical and m is 1 or 2; R₂ is

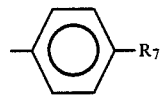

wherein R₇ has the same meanings as R₁ except that R₇ and R₁ cannot simultaneously be the same and, when R₁ is a radical as aforesaid other than hydrogen, R₂ can be alkyl of 1 to 4 carbon atoms; R₃ is cyclopentyl or hydroxycyclopentyl; R₄ is hydrogen or hydroxy and n is 0 to 3, or a non-toxic pharmaceutically acceptable salt or ester thereof.

* * * * *